(12) United States Patent
Joshi et al.

(10) Patent No.: US 8,277,840 B2
(45) Date of Patent: Oct. 2, 2012

(54) SUSTAINED RELEASE FORMULATION OF ALPRAZOLAM

(75) Inventors: Manjusha Joshi, Maharashtra (IN); Ganesh Vinayak Gat, Maharashtra (IN); Satish Ramanlal Mehta, Maharashtra (IN)

(73) Assignee: Emcure Pharmaceuticals Limited, Pune, Maharashtra (IN)

( * ) Notice: Subject to any disclaimer, the term of this patent is extended or adjusted under 35 U.S.C. 154(b) by 628 days.

(21) Appl. No.: 11/996,377

(22) PCT Filed: Jul. 20, 2006

(86) PCT No.: PCT/IB2006/001987
§ 371 (c)(1),
(2), (4) Date: Aug. 18, 2008

(87) PCT Pub. No.: WO2007/010369
PCT Pub. Date: Jan. 25, 2007

(65) Prior Publication Data
US 2008/0311193 A1    Dec. 18, 2008

(30) Foreign Application Priority Data
Jul. 22, 2005 (IN) .......................... 880/MUM/2005

(51) Int. Cl.
*A61K 9/22* (2006.01)

(52) U.S. Cl. ......... 424/468; 424/465; 424/482; 514/220
(58) Field of Classification Search .................. None
See application file for complete search history.

(56) References Cited

U.S. PATENT DOCUMENTS

| | | | |
|---|---|---|---|
| 3,109,843 A | 11/1963 | Reeder et al. | |
| 3,849,434 A | 11/1974 | Llewellyn et al. | |
| 3,987,052 A | 10/1976 | Hester, Jr. | |
| 2003/0190354 A1 | 10/2003 | Sela | |
| 2004/0006072 A1 | 1/2004 | Franz et al. | |
| 2004/0009220 A1 | 1/2004 | Sharma | |
| 2004/0009971 A1 | 1/2004 | Wong | |

OTHER PUBLICATIONS

Robert O. Williams, III et al; "Method to Recover a Lipophilic Drug From Hydroxypropyl Methylcellulose Matrix Tablets", AAPS Pharmscitech, 2001 2(2), article 8 pp. 1-9.
Remington's Pharmaceutical Sciences Eithteenth Edition, 1990, pp. 1677-1679.
Physicians' Desk Reference, PDR 58 Edition, 2004.
"Oral extended-release products", Australian Prescriber vol. 22, No. 4, 1999.

*Primary Examiner* — Robert A Wax
*Assistant Examiner* — Hasan S. Ahmed
(74) *Attorney, Agent, or Firm* — Ladas & Parry LLP (57) ABSTRACT

The present invention is directed towards the preparation of extended release Alprazolam formulation. The formulation thus obtained provides an efficient mode of delivery of Alprazolam in a continuous manner.

13 Claims, 2 Drawing Sheets

SUSTAINED RELEASE FORMULATION OF ALPRAZOLAM

FIELD OF THE INVENTION

The present invention provides a novel sustained release composition comprising alprazolam.

INTRODUCTION

Benzodiazepines are a class of compounds, commonly known as tranquillizers and sleeping pills. Benzodiazepines are minor tranquillizers that affect the central nervous system by slowing down the body physically, mentally and emotionally as referred in U.S. Pat. No. 3,849,434. The benzodiazepines act upon the central nervous system to reduce communication between certain neurons, lowering the level of activity in the brain. The benzodiazepines are a class of drugs with sedatives, anticonvulsant, and muscle relaxant properties as referred in U.S. Pat. No 3,109,843 including hypnotic and amnestic properties. Benzodiazepines are often used for short-term relief of severe, disabling anxiety or insomnia. The most common benzodiazepines prescribed are XANAX® (Alprazolam), VALIUM ® (Diazepam), SEREPAX ® (Oxazepam), and Temazepam. Benzodiazepines act as CNS inactivators.

Alprazolam i.e. (8-chloro-1-methyl-6-phenyl-4H-s-triazolo[4,3-a][1,4]) benzodiazepine, which has been cited in U.S. Pat. No. 3,987,052. According to the USFDA approval of alprazolam is used for the treatment of anxiety disorders and panic attacks. Anxiety disorders are characterized by unrealistic worry and apprehension, causing symptoms of restlessness, aches, trembling, shortness of breath, smothering sensation, palpitations, sweating, cold clammy hands, lightheadedness, flushing, exaggerated startle responses, problems concentrating, and insomnia. Panic attacks occur either unexpectedly or in certain situations (i.e. driving), and can require higher dosages of alprazolam. XANAX® (Alprazolam) is also used in the treatment of panic disorder, which appears as unexpected panic attacks and may be accompanied by a fear of open spaces called agoraphobia.

The immediate-release Alprazolam tablet formulation is currently marketed as XANAX® (Alprazolam) tablets by PHARMACIA AND UPJOHN. (Ref: http://www.accessdata.fda.govsripts/cder/drugsatfda/). XANAX® (Alprazlam) is delivered as an oral tablet With various strengths like 0.25 mg, 0.5 mg, 1 mg and 21 mg.

The extended-release Alprazolam tablet formulation is currently marketed as

XANAX® (Alprazolam) XR tablets by PHARMACIA AND UPJOHN. (Ref: http://www.accessdata.fda.gov/scripts/cder/drugsatfda/). These tablets are marketed as an oral tablet in the dose strengths of 0.5 mg, 1mg, 2 mg, and 3 mg.

BACKGROUND OF THE INVENTION

Alprazoalm can be delivered via two methods. The first one being the immediate release mode. The immediate-release Alprazolam (XANAX® (Alprazolam)) can be prescribed for administration of up to four doses per day for treatment of anxiety and, in some instances, in excess of four doses per day for treatment of panic disorders disclosed in US 2004/0006072A1. However, such frequency of dosing is bothersome and can adversely affect patient stability. Further, breakthrough anxiety can be a problem in current dosing methods.

The non immediate-release delivery systems may be broadly divided into following categories. (Ref: Remington's Pharmaceutical Sciences, 18$^{th}$ Edition, Mack Publishing Company, Page 1677)

a) Delayed release: These release systems are those, which use repetitive, intermittent dosings of a drug from one or more immediate release units incorporated into a single dosage form. This release system provides a patient compliance, however, it does not produce or maintain uniform drug blood levels within the therapeutic range.

b) Site-Specific and receptor release: This release system refers to a targeting of a drug directly to a certain biological location.

c) Sustained-release: This system includes any drug delivery system that achieves slow release of drug-over an extended period of time. If the system is successful at maintaining constant drug levels in the blood or target tissue, it is considered a controlled-release system. If it is unsuccessful at this, but extends the duration of action over that achieved by conventional delivery, it is considered a prolonged release system.

XANAX® (Alprazolam) tablet, which is an immediate release formulation of Alprazolam, are designated to be divided by the patient into equally sized portions for dose control as disclosed in Physicians Desk Reference, 58.sup.th edition (2004), pp 2798-2802. The immediate release tablet needs to be taken at frequent intervals. The shortcoming faced in the immediate release is maintaining the drug concentration in the blood level. As the drug level is not maintained, there exists peaks and trough phenomena. Further, once the drug level descends down, during the trough interval, the panic attacks during this interval might create problems as referred patent US 2004/0006072 A1. Moreover, the peak and trough delivery pattern provided by known dosage forms result in undesirable effects, such as sedation due to over dose of medication when reached at the peak point in the beginning, memory impairment and abuse potential.

The dividing of the dose is generally not appropriate for extended release dosage forms that are usually designed to administer as a while. However, there exists a shortcoming with the alprazolam extended-release dosage from i.e. a wide range of dosage amount is prescribable, depending upon the nature and the severity being treated. Further, certain treatment regimens require different dosage amounts to be administered on different days. Further extended release products contain a higher drug load and thus any loss of integrity of the release characteristics of the dosage forms has a potential problem The release rate can also be altered by various factors including food and the rate of transit through the gut.

Hence, it would be of great benefit to provide a sustained release alprazolam formulation system that is adaptable to a broad range of dosage strengths, yet exhibits substantial bioequivalence, when different dosage strengths are administered in an equal total dosage amount. One approach to solve this problem would be to provide all dosage strengths in an identical formulation, wherein higher dosage strengths are accommodated in proportionally larger dosage units. However, it is found preferable to provide all dosage strengths in tablets of similar total weight. This facilitates the avoidance of excessively small tablets for the lower dosage strengths, and excessively large tablets for higher dosage strengths.

A good drug delivery system is expected to provide efficient delivery to target tissue, steady therapeutic concentrations and minimizing exposure to nontarget tissue. It is also possible to reduce the dose or frequency and to improve compliance. The systems can enhance the therapeutic ratio and regimens of many existing agents that would not be useful in conventional dosage forms because of their toxicity or short half-lives. In this manner, a drug treatment is achieved, whose criteria are (a) better efficacy, (b) selectivity and (c) safety.

Further, there remains a need for an effective dosage form that provides a release of alprazolam over a period of time, which would cause a reduction in side effects associated with alprazolam dosings.

Thus, a sustained-release formulation system for alprazolam is desired that accommodates dosage strengths over at least a six fold range from 0.5 mg to 3 mg in substantially the same total dosage form weight, yet exhibits bioequivalence over a corresponding range of excipient/drug weight ratios.

An approach to solve this problem would be to identify for a sustained-release dosage form utilizing an HPMC matrix, a suitable amount of mix of HPMC giving substantially equivalent in vivo release and absorption rates over a broad range of alprazolam loadings as referred in patent application US 20040006072. Though mentioned therein, the only exemplified total weight of HPMC is 121.2 mg, having 1:1 ratio only. Surprisingly, in our hand, we found that the in-vitro profile of the composition prepared according to US 2004/0006072 when compared with XANAX® (Alprazolam) XR, the Standard Deviation (SD) as well as % Relative Standard Deviation (% RSD) showed substantially high figures. These substantially high figures relates to the high degree of fluctuations in the said composition comparative to XANAX® (Alprazolam) XR, thus creating a demand for providing a better sustained release composition.

Currently available alprazolam compositions do not provide the desired pharmaceutical effect. Hence, there is a need for providing better sustained release compositions.

The use of lower quantities of (a) K4M HPMC and (b) K100LVP HPMC gives comparatively better results with respect to drug release. Due to the same, there are less fluctuations in % related standard deviation. Hence, the pharmaceutical composition prepared according to the current invention is superior to the prior are compositions.

The dissolution profile in biological system is reflected from in-vitro dissolution results. It is advisable to have better pharmaceutical composition having less fluctuations, which are inturn dependent on the in-vitro dissolution profile. Thus, the pharmaceutical composition according to the current embodiment is advantageous and better for patients as compared to the prior art compositions.

OBJECT OF THE INVENTION

The object of the invention is to provide an efficient mode of delivery of Alprazolam.

SUMMARY OF THE INVENTION

According to the present invention, the efficient mode of extended release of Alprazolam is obtained by making use of less quantities of HPMC's. Thus, by making use of the same, Alprazolam formulation is obtained, which has less fluctuations in % related standard deviation as compared to the prior art compositions.

BRIEF DESCRIPTION OF THE DRAWING

The subject matter of the invention is described in more detail herein after in connection with the exemplary embodiments illustrated in the drawing.

This figure refers to the dissolution profile of 3 mg tablet (prepared according to experiment discussed in Example 13), which indicates the comparative % dissolution data for 24 hours. The graph of time interval in hours on the X axis vs the % release on the Y axis is plotted.

This figure refers to the dissolution profile of 2 mg tablet (prepared according to experiment discussed in Example 10), which indicates the graphical representation of % dissolution data of Emcure's tablet for 24 hours. The graph of time interval in hours on the X axis vs the % release on the Y axis is plotted.

This figure refers to the dissolution profile of 1 mg tablet (prepared according to experiment discussed in Example 12), which indicates the graphical representation of % dissolution data of Emcure's tablet for 24 hours. The graph of time interval in hours on the X axis vs the % release on the Y axis is plotted.

DETAILED DESCRIPTION OF THE INVENTION

Figure 1:
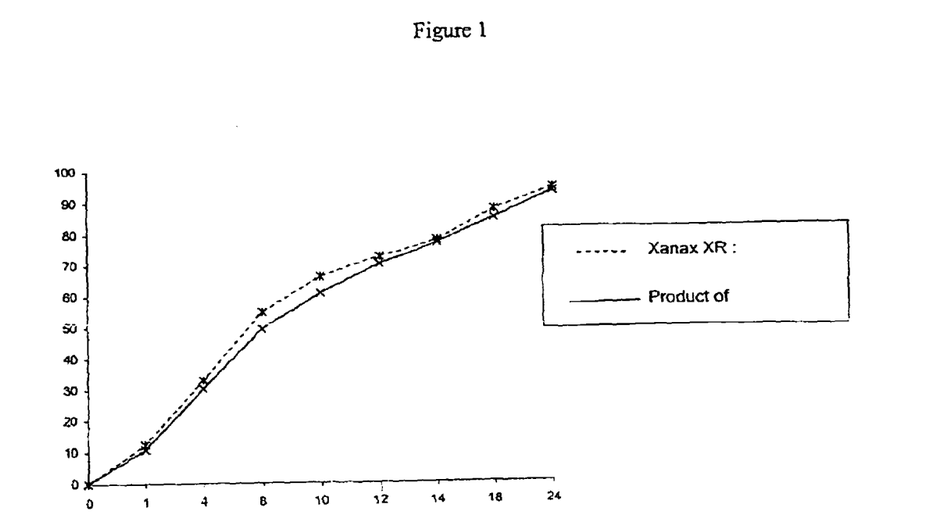
FIG. 1: Dissolution Profile of XANAX® (Alprazolam) Xr vs Product of example 13 (3 mg Alprazolam)
Figure 2:
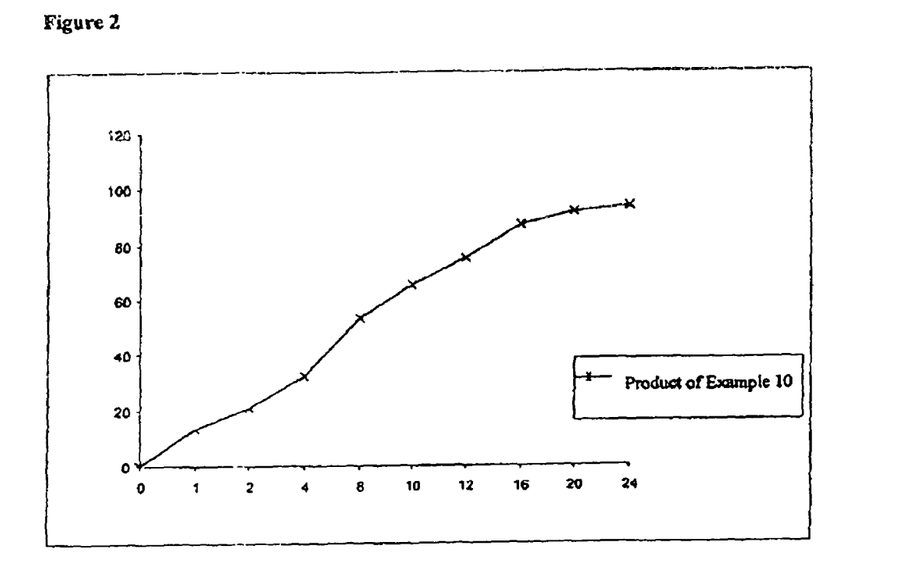
FIG. 2: Dissolution Profile of XANAX® (Alprazolam) Xr vs Product of example 10 (2 mg Alprazolam).
Figure 3:
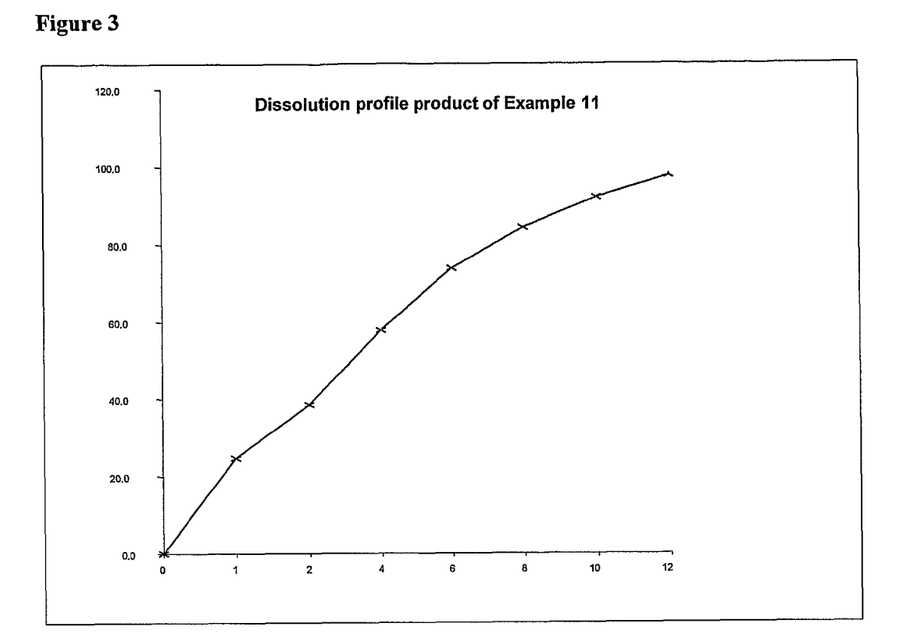
FIG. 3: Dissolution Profile of XANAX® (Alprazolam) Xr vs Product of example 11 (0.5 mg Alprazolam) and This figure refers to the dissolution profile of 0.5 mg tablet (prepared according to experiment discussed in Example 11), which indicates the graphical representation of % dissolution data of Emcure's tablet for 24 hours. The graph of time interval in hours on the X axis vs the % release on the Y axis is plotted.
Figure 4:
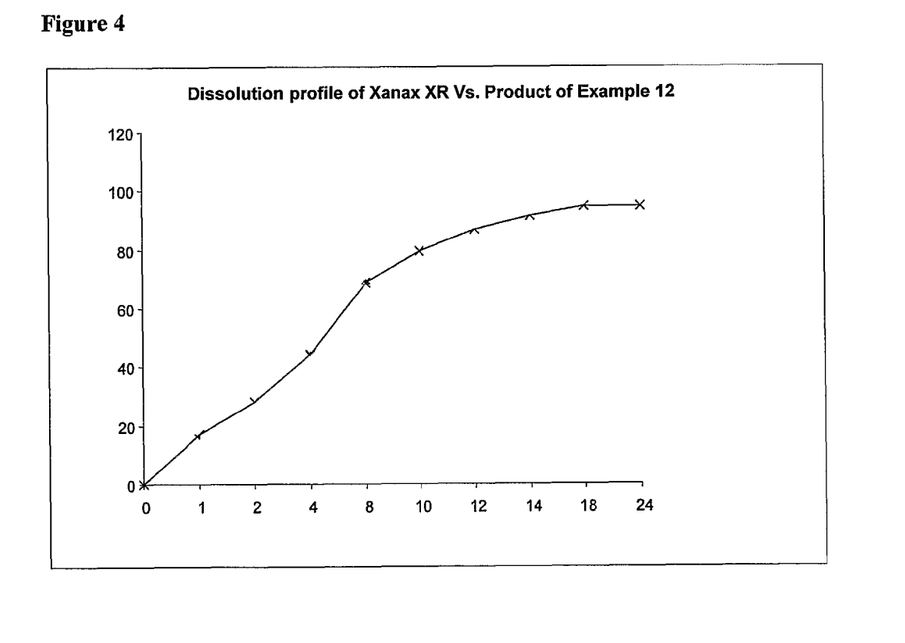
FIG. 4: Dissolution Profile of XANAX® (Alprazolam) Xr vs Product of example 12 (1 mg Alprazolam)

Alprazolam i.e. (8-chloro-1-methyl-6-phenyl-4H-s-triazolo[4,3-a][1,4]) benzodiazepine, is cited in U.S. Pat. No. 3,987,052. It is well known in the prior art that the alprazolam is used in treatment of anxiety disorders and panic attacks. The immediate release formulation of alprazolam however, has certain disadvantages of peak and trough phenomena. The frequency of dosings is also more in case of immediate release tablets.

Accordingly, the invention provides a sustained release pharmaceutical composition comprising:
(a) a therapeutically effective amount of alprazolam,
(b) a high viscosity hydroxy-propyl-methyl cellulose (HPMC) and low viscosity hydroxy-propyl-methyl cellulose (HPMC) in a ratio of 65:35 to 85:15, and
(c) pharmaceutically acceptable excipients.

The tablet of present invention contains alprazolam, distributed in a matrix that comprises HPMC(s) and other excipients as discussed herein.

Hydroxy propyl methylcellulose, being a semi-synthetic material derived from cellulose, is a linear polymer comprised of etherified anhydrous glucose rings. There are broadly two types of HPMC viz high viscosity polymer and low viscosity polymer. Use of High viscosity polymer retards the rate of release to higher extent, whereas the use of low viscosity polymer retards the rate of release to comparatively lower extent. Furthermore, combination of both types of HPMCs or single type of HPMC is used depending upon the release pattern of interest.

To prevent a tablet from immediately disintegrating a fast rate of hydration followed by quick gelation is necessary for a rate controlling polymer to form a protective gelatinous layer around the matrix. The critical parameters of fast polymer hydration and gel layer formation are considered in case of a water-soluble drug and water-soluble excipients.

HPMC is commercially available in various grades, under several trade names, including Methocel® E, F, J and K of dow chemicals, HPM of British Celanese Ltd., U.K., and Metalose® SH of Shin-Etsu Ltd., Japan. The two polymer grades of METHOCEL most commonly used in controlled-release applications are K(HPMC 2208, USP) and E(HPMC 2910, USP). F-chemistry products (HPMC 2906, USP) are used less commonly. The various grades available under a given trade name typically represent differences in methoxy and hydropropoxy content as well as molecular weight of HPMC. The preferred HPMC, used for the retardation purpose is HPMC 2208, which contains about 19% to about 24% by weight of methoxy substituents, and about 4% to about 12% by weight of hydroxypropoxy substituents, calculated on a dry basis.

In one aspect of the present invention, combination of both HPMCs i.e. (a) HPMC having high viscosity and (b) HPMC having low viscosity have been used. The term "high viscosity HPMC" herein refers to HPMC having a viscosity of about 1,500 to about 2,25,000 cP, and the term "low viscosity HPMC" herein refers to HPMC having a viscosity of about 2 to about 400 cP.

The high viscosity grade polymers available are METHOCEL K4M Premium, K15M Premium, and K100M Premium. Preferred high viscosity HPMC is HPMC 2208 having a viscosity of about 3000 to about 5600 cP, which is illustratively available as Methocel® K4 MP of Dow. Equivalent products are available from other sources as well.

The low viscosity grade polymers available are K3P LV and K 100P LV. The preferred low viscosity HPMC is HPMC 2208 having a viscosity of about 80 to about 120 cP, which is illustratively available as Methocel® K100LVP of Dow. Equivalent products are available from other sources as well.

Our invention makes use of Methocel® K4 MP of Dow as a high viscosity polymer and a Methocel® K100LVP of Dow as a low viscosity polymer. US 2004/0006072 discloses the high viscosity HPMC to low viscosity HPMC to be 60:40 to 40:60. In our embodiment, both high viscosity and low visocity HPMC are present in the particular composition ranging from about 65:35 to 85:15. The preferred ratio being 65:35 to 75:25. The most preferred ratio being 70:30. Further, the total amount of HPMC used is also less as compared to patent application US 2004/0006072. US 2004/0006072 claims the total polymer weight to be of about 110 to 135 mg. However, we use about 70 to 100 mg. of the polymer thus making our invention cost effective. The preferred range for the weight of the polymer in the tablet is 75 to 90 mg.

It may be noted that the ratio of mix of HPMC, as well as having different total weight of mix of HPMC gives the interesting results, which are better than the immediate release profile, which eliminates the problems associated with peak and trough issue.

The use of lower quantities of (a) K4M HPMC and (b) K100LVP HPMC gives comparatively better results to the said pharmaceutical composition, such as with respect to drug release. Due to the same, there are less fluctuations in % related standard deviation. Hence, the pharmaceutical composition prepared according to the current invention is superior to the prior art compositions.

The dissolution profile in biological system is reflected from in-vitro dissolution results. It is advisable to have better pharmaceutical composition having less fluctuations, which are in turn dependent on the in-vitro dissolution profile. Thus, the pharmaceutical composition according to the current embodiment is advantageous and better for patients.

The other excipient used in our tablet invention is lactose. Lactose is used as a preferred diluent. Lactose is widely used as a filler or filler-binder in the manufacture of pharmaceutical tablets and capsules. The general properties of lactose which make a contribution to its usage in formulation are (a) cost effectiveness, (b) easy availability, (c) low hygroscopicity, (d) compatibility with the active ingredients, (e) stability, (f) water solubility etc. Lactose monohydrate is used in one of the embodiment. The amount of lactose used in our invention is about 300 mg for 3 mg of alprazolam. Alprazolam is primarily mixed with lactose and then the further processing is done.

Magnesium stearate is an excipient, which is used as a lubricant, to prevent the compacted powder mass from sticking to the equipment during the tabletting or encapsulation process and allow easy ejection of the tablet during tablet formation. However, over lubrication may result into coating of the hydrophobic material on the tablet and thereby retard the release rate. Hence, an appropriate amount of Magnesium Stearate is necessary.

In another embodiment colloidal silicon dioxide is used. The most commonly used "glidant" in solid oral dosage form formulations is colloidal silicon dioxide; also know by the trade names of Cab-o-Sil or Aerosil. This material is extremely effective in improving the overall flow characteristics of a blend by coating the surfaces of its' components thereby reducing their inter-particulate friction.

The colouring agents optionally can be added at the appropriate stage of preparation of pharmaceutical composition in suitable quantities. It can be along with the lactose. The said colouring agents can be selected from any pharmaceutically acceptable colouring agents. The preferred colouring agents are Lake green blend LB-51426 or D & C Yellow No 10.

The ingredients can be sifted independently or in combination with other ingredients, at the appropriate stage.

According to the present invention, the strength of sustained release tablets of alprazolam is in the range of 0.5 mg to 3.0 mg equivalent to base.

ADVANTAGES

The advantages of the sustained release composition prepared according to the invention are as under:

i. The composition provides a convenient method of delivery of alprazolam and avoids the frequency of dosages taken by the patient.

ii. The composition provides a mode of release of alprazolam that is adaptable to a broad range of dosage strengths.

iii. The composition delivers alprazolam in a continuous manner so that the peak and trough phenomena would be practically inexistent iv. The composition provides alprazolam in such a dosage that the drug concentration in the blood is maintained for a longer period of time v. The composition makes use of the high viscosity and low viscosity HPMC in such a weight ratio so as to avoid bioequivalent fluctuations.

vi. The invention provides a process for the preparation of Alprazolam formulation which is simple, having less number of steps, involving less man power, having smaller time cycle, providing good yields, with a good purity profile, industrially feasible and economical.

vii. The invention reduces the total quantities of HPMC and making the process cost effective and industrial friendly.

The sustained release tablets according to the instant invention are prepared according to the following process steps comprising of;

a) Mixing Alprazolam with lactose and optionally the coloring agents in geometric proportion.
b) Sifting the mixture to obtain the homogeneous blend.
c) Adding HPMC K-4M and HPMC K-100 LVP to the blend from step (b) and mixing to get a homogenous blend.
d) Granulating the blend with water.
e) Drying the wet mass.
f) Reducing the size of dried granules followed by lubrication and
g) compressing to form tablet.

The dissolution procedure for the tablets can be carried out as per the procedure known in the art using following parameters.

Experimental Procedure of Dissolution Test for the Comparative Study

The dissolution is carried out by using following parameters

| | |
|---|---|
| Medium | Mixed Phosphate Buffer pH 6.0 ± 0.1 |
| Volume | 500 ml |
| Apparatus | USP I (Basket) |
| Speed | 100 rpm |
| Temperature | 37.0° C. |
| Time Interval | 1 Hr, 4 Hr, 8 Hr, 10 Hr, 12 Hr, 14 Hr, 18 Hr, 24 Hr. |
| Withdrawal volume | 5 ml |

The principles, preferred embodiments, and modes of operation of the present invention have been described in the foregoing specification. The invention which is intended to be protected herein, however, is not to be construed limited to the particular forms disclosed, since these are to be regarded as illustrative rather than restrictive. Variations and changes may be made by those skilled in the art, without departing from the spirit of the invention.

The present invention is more particularly illustrated in the following example(s), but is not to limit the scope of the present invention.

EXAMPLE 1

70:30; 90 mg Polymer

Tablets having the tabulated composition were prepared by the procedure, mentioned above.

Alprazolam was mixed with Lactose* in geometric proportion. The mixture was sifted to obtain the homogeneous blend. HPMC K-4M and HPMC K-100 LVP were added to the above blend and mixed to get a homogenous blend. The blend was granulated with water. The wet mass was dried. The size of dried granules was reduced followed by lubrication and was compressed to form a tablet.

Optionally the coloring agent(s) are added, if required. In Example 1, the coloring agents are not added.

TABLE 1

| SERIAL NUMBER | INGREDIENTS | WEIGHT (mg) |
|---|---|---|
| 1 | Alprazolam | 3.0 |
| 2 | Lactose monohydrate USPNF | 248.25 |
| 3 | Hydroxy Propyl Methyl Cellulose K-4M | 63.0 |
| 4 | Hydroxy Propyl Methyl Cellulose K-100 LVP | 27.0 |
| 5 | Colloidal Silicon Dioxide (Aerosil-200)USPNF | 0.75 |

TABLE 1-continued

| SERIAL NUMBER | INGREDIENTS | WEIGHT (mg) |
|---|---|---|
| 6 | Magnesium Stearate USPNF | 3.00 |
| 7 | Purified Water | q.s. |
| | Total weight | 345 |

EXAMPLE 2

70:30; 90 mg Polymer

Tablets having the tabulated composition were prepared by the procedure, mentioned above.

TABLE 2

| SERIAL NUMBER | INGREDIENTS | WEIGHT (mg) |
|---|---|---|
| 1 | Alprazolam | 3.0 |
| 2 | Lactose monohydrate USPNF | 247.19 |
| 3 | Hydroxy Propyl Methyl Cellulose K-4M | 63.0 |
| 4 | Hydroxy Propyl Methyl Cellulose K-100 LVP | 27.0 |
| 5 | Colloidal Silicon Dioxide (Aerosil-200)USPNF | 0.75 |
| 6 | Magnesium Stearate USPNF | 3.00 |
| 7 | Purified Water | q.s. |
| 8 | Green Color | 0.35 |
| | Total weight | 344.29 |

The obtained dissolution profile

TABLE 3

| Time | EMCURE-SR (90 mg, Ratio 70:30) |
|---|---|
| 0 | 0 |
| 1 | 10.86 |
| 2 | 17.95 |
| 4 | 28.36 |
| 8 | 44.82 |
| 10 | 52.24 |
| 12 | 57.89 |
| 14 | 62.86 |
| 18 | 70.51 |
| 24 | 78.12 |

EXAMPLE 3

65:35; 80 mg Polymer

Tablets having the tabulated composition were prepared by the procedure, as mentioned above.

TABLE 4

| SERIAL NUMBER | INGREDIENTS | WEIGHT (mg) |
|---|---|---|
| 1 | Alprazolam | 3.0 |
| 2 | Lactose monohydrate USPNF | 258.25 |
| 3 | Hydroxy Propyl Methyl Cellulose K-4M | 52 |
| 4 | Hydroxy Propyl Methyl Cellulose K-100 LVP | 28 |
| 5 | Colloidal Silicon Dioxide | 0.75 |
| 6 | Magnesium Stearate | 3.00 |
| 7 | Purified Water | q.s. |
| | Total weight | 345 |

The obtained dissolution profile

TABLE 5

| Time | XANAX® (Alprazolam)-SR | EMCURE-SR |
|---|---|---|
| 0 | 0 | 0 |
| 1 | 12.80 | 14.5 |
| 2 | 21.80 | 23.4 |
| 4 | 35.0 | 37.2 |
| 8 | 54.90 | 60.8 |
| 10 | 63.7 | 73.1 |
| 12 | 70.4 | 86.4 |
| 14 | 81.6 | 93.9 |
| 18 | 86.8 | 101.9 |
| 24 | 90.7 | 103.8 |

EXAMPLE 4

70:30; 80 mg Polymer

Tablets having the tabulated composition were prepared by the procedure as mentioned above.

TABLE 6

| SERIAL NUMBER | INGREDIENTS | WEIGHT (mg) |
|---|---|---|
| 1 | Alprazolam | 3.0 |
| 2 | Lactose monohydrate USPNF | 258.25 |
| 3 | Hydroxy Propyl Methyl Cellulose K-4M | 56 |
| 4 | Hydroxy Propyl Methyl Cellulose K-100 LVP | 24 |
| 5 | Colloidal Silicon Dioxide | 0.75 |
| 6 | Magnesium Stearate | 3.00 |
| 7 | Purified Water | q.s. |
| | Total weight | 345 |

The obtained dissolution profile

TABLE 7

| Time | EMCURE-SR |
|---|---|
| 0 | 0 |
| 1 | 10.7 |
| 2 | 18.2 |
| 4 | 29.3 |
| 8 | 48.8 |
| 10 | 60.5 |
| 12 | 67.4 |
| 14 | 77.9 |
| 18 | 84.2 |
| 24 | 88.0 |

EXAMPLE 5

75:25; 80 mg Polymer

Tablets having the tabulated composition were prepared by procedure, as mentioned above.

TABLE 8

| SERIAL NUMBER | INGREDIENTS | WEIGHT (mg) |
|---|---|---|
| 1 | Alprazolam | 3.0 |
| 2 | Lactose monohydrate USPNF | 258.25 |
| 3 | Hydroxy Propyl Methyl Cellulose K-4M | 60 |
| 4 | Hydroxy Propyl Methyl Cellulose K-100 LVP | 20 |
| 5 | Colloidal Silicon Dioxide | 0.75 |
| 6 | Magnesium Stearate | 3.00 |
| 7 | Purified Water | q.s. |
| | Total weight | 345 |

The obtained dissolution profile

TABLE 9

| Time | EMCURE-SR |
|---|---|
| 0 | 0 |
| 1 | 13.6 |
| 2 | 21.3 |
| 4 | 32.7 |
| 8 | 54.1 |
| 10 | 65.4 |
| 12 | 73.7 |
| 14 | 83.8 |
| 18 | 88.9 |
| 24 | 91.3 |

EXAMPLE 6

70:30; 100 mg Polymer

Tablets having the tabulated composition were prepared by the procedure, as mentioned above.

TABLE 10

| SERIAL NUMBER | INGREDIENTS | WEIGHT (mg) |
|---|---|---|
| 1 | Alprazolam | 3.0 |
| 2 | Lactose monohydrate USPNF | 238.25 |
| 3 | Hydroxy Propyl Methyl Cellulose K-4M | 70 |
| 4 | Hydroxy Propyl Methyl Cellulose K-100 LVP | 30 |
| 5 | Colloidal Silicon Dioxide | 0.75 |
| 6 | Magnesium Stearate | 3.00 |
| 7 | Purified Water | q.s. |
| | Total weight | 345 |

The obtained dissolution profile

TABLE 11

The obtained dissolution profile:

| Time | EMCURE-SR |
|---|---|
| 0 | 0 |
| 1 | 11.42 |
| 4 | 28.11 |
| 8 | 45.06 |
| 10 | 55.01 |
| 12 | 64.67 |
| 14 | 72.93 |
| 18 | 85.56 |
| 24 | 96.22 |

EXAMPLE 7

Direct Compression Experiment

70:30; 80 mg Polymer

Tablets having the tabulated composition were prepared by the procedure, as mentioned above.

TABLE 12

| SERIAL NUMBER | INGREDIENTS | WEIGHT (mg) |
|---|---|---|
| 1 | Alprazolam | 3.0 |
| 2 | Lactose monohydrate USPNF | 258.25 |
| 3 | Hydroxy Propyl Methyl Cellulose K-4M | 56 |
| 4 | Hydroxy Propyl Methyl Cellulose K-100 LVP | 24 |
| 5 | Colloidal Silicon Dioxide | 0.75 |
| 6 | Magnesium Stearate | 3.00 |
| 7 | Purified Water | q.s. |
| | Total weight | 345 |

The obtained dissolution profile

TABLE 13

| Time | EMCURE-SR |
|---|---|
| 0 | 0 |
| 1 | 16.9 |
| 2 | 27.4 |
| 4 | 44.7 |
| 8 | 67.9 |
| 10 | 79.6 |
| 12 | 87.1 |
| 14 | 94.4 |
| 18 | 96.7 |
| 24 | 96.5 |

EXAMPLE 8

Making Use of Just K4M HPMC

80:0; 80 mg Polymer

Tablets having the tabulated composition were prepared by the procedure, as mentioned above.

TABLE 14

| SERIAL NUMBER | INGREDIENTS | WEIGHT (mg) |
|---|---|---|
| 1 | Alprazolam | 3.0 |
| 2 | Lactose monohydrate USPNF | 258.25 |
| 3 | Hydroxy Propyl Methyl Cellulose K-4M | 80 |
| 4 | Hydroxy Propyl Methyl Cellulose K-100 LVP | — |
| 5 | Colloidal Silicon Dioxide | 0.75 |
| 6 | Magnesium Stearate | 3.00 |
| 7 | Purified Water | q.s. |
| | Total weight | 345 |

TABLE 15

| Time | EMCURE-SR |
|---|---|
| 0 | 0 |
| 1 | 10.1 |
| 2 | 16.7 |
| 4 | 26.2 |
| 8 | 40.4 |
| 10 | 48.7 |
| 12 | 55.6 |
| 14 | 65.7 |
| 18 | 73.2 |
| 24 | 77.3 |

EXAMPLE 9

Making Use of Just K 100 LVP HPMC

0:80; 80 mg Polymer

Tablets having the tabulated composition were prepared by the procedure as mentioned above.

TABLE 16

| SERIAL NUMBER | INGREDIENTS | WEIGHT (mg) |
|---|---|---|
| 1 | Alprazolam | 3.0 |
| 2 | Lactose monohydrate USPNF | 258.25 |
| 3 | Hydroxy Propyl Methyl Cellulose K-4M | |
| 4 | Hydroxy Propyl Methyl Cellulose K-100 LVP | 80 |
| 5 | Colloidal Silicon Dioxide | 0.75 |
| 6 | Magnesium Stearate | 3.00 |
| 7 | Purified Water | q.s. |
| | Total weight | 345 |

TABLE 17

| Time | EMCURE-SR |
|---|---|
| 0 | 0 |
| 1 | 17.3 |
| 2 | 33.5 |
| 4 | 65.5 |
| 8 | 88.2 |
| 10 | 91.2 |
| 12 | 90.7 |
| 14 | 89.9 |
| 18 | 89.0 |
| 24 | 87.4 |

EXAMPLE 10

70:30; 80 mg Polymer; 2.00 mg Alprazolam

Tablets having the tabulated composition were prepared by the procedure, as mentioned above.

TABLE 18

| SERIAL NUMBER | INGREDIENTS | WEIGHT (mg) |
|---|---|---|
| 1 | Alprazolam | 2.0 |
| 2 | Lactose monohydrate USPNF | 259.25 |
| 3 | Hydroxy Propyl Methyl Cellulose K-4M | 56.00 |
| 4 | Hydroxy Propyl Methyl Cellulose K-100 LVP | 24.00 |

TABLE 18-continued

| SERIAL NUMBER | INGREDIENTS | WEIGHT (mg) |
|---|---|---|
| 5 | Colloidal Silicon Dioxide | 0.75 |
| 6 | Magnesium Stearate | 3.00 |
| | Total weight | 345 |

TABLE 19

| Time | EMCURE-SR |
|---|---|
| 0 | 0 |
| 1 | 13.3 |
| 2 | 20.7 |
| 4 | 32.3 |
| 8 | 53.6 |
| 10 | 65.6 |
| 12 | 75.0 |
| 16 | 87.3 |
| 20 | 91.7 |
| 24 | 93.8 |

EXAMPLE 11

70:30; 80 mg Polymer; 0.50 mg Alprazolam

Tablets having the tabulated composition were prepared by the procedure as mentioned above.

TABLE 20

| SERIAL NUMBER | INGREDIENTS | WEIGHT (mg) |
|---|---|---|
| 1 | Alprazolam | 0.50 |
| 2 | Lactose monohydrate USPNF | 260.75 |
| 3 | Hydroxy Propyl Methyl Cellulose K-4M | 56.00 |
| 4 | Hydroxy Propyl Methyl Cellulose K-100 LVP | 24.00 |
| 5 | Colloidal Silicon Dioxide | 0.75 |
| 6 | Magnesium Stearate | 3.00 |
| | Total weight | 345 |

TABLE 21

| Time | EMCURE-SR |
|---|---|
| 0 | 0.0 |
| 1 | 24.6 |
| 2 | 38.5 |
| 4 | 57.8 |
| 6 | 73.7 |
| 8 | 84.3 |
| 10 | 91.9 |
| 12 | 97.6 |
| 20 | 91.7 |
| 24 | 93.8 |

Conclusion: The dissolution profile when compared with XANAX® (Alprazolam) showed a comparable release pattern.

EXAMPLE 12

70:30; 80 mg Polymer, 1.00 mg Alprazolam

Tablets having the tabulated composition were prepared by the procedure, as mentioned above.

Color was mixed with some part of lactose and sifted through 100#mesh Alprazolam was mixed with lactose in geometric proportion and sifted through 40 mesh. HPMC K-4M and HPMC K-100 LVP are sifted through 40 mesh and mixed with above blend. This homogenous blend was granulated with water to form wet mass. Wet mass was dried and then crushed to form dried granules. Dried granules were lubricated and compressed to tablet with suitable punches.

TABLE 22

| SERIAL NUMBER | INGREDIENTS | WEIGHT (mg) |
|---|---|---|
| 1 | Alprazolam | 1.0 |
| 2 | Lactose monohydrate USPNF | 260.00 |
| 3 | Hydroxy Propyl Methyl Cellulose K-4M | 56.00 |
| 4 | Hydroxy Propyl Methyl Cellulose K-100 LVP | 24.00 |
| 5 | Colloidal Silicon Dioxide | 0.75 |
| 6 | Magnesium Stearate | 3.00 |
| 7 | D&C Yellow No. 10 | 0.25 |
| 8 | Purified Water | q.s. |
| | Total weight | 345 |

TABLE 23

| Time | EMCURE-SR |
|---|---|
| 0 | 0 |
| 1 | 17.3 |
| 2 | 28.2 |
| 4 | 44.3 |
| 8 | 68.9 |
| 10 | 79.3 |
| 12 | 86.6 |
| 14 | 91.2 |
| 18 | 94.6 |
| 24 | 94.6 |

According to the instant invention, the Alprazolam ER tablets are prepared as per Example Number 4. The dissolution experiments of the said tablets was carried out. Exactly similar dissolution experiment was carried out with respect to the Alprazolam ER tablets obtained from the public domain i.e XANAX® (Alprazolam) XR of Pharmacia Upjon; Batch No. 63 MCX.

The experimental procedure and results of the above experiments is provided below in Table-25 and Table-26.

Experimental Procedure for the Preparation of Product of Example 13

TABLE 24

| SERIAL NUMBER | INGREDIENTS | WEIGHT (mg) |
|---|---|---|
| 1 | Alprazolam | 3.0 |
| 2 | Lactose monohydrate USPNF | 257.9 |
| 3 | Hydroxy Propyl Methyl Cellulose K-4M | 56.0 |
| 4 | Hydroxy Propyl Methyl Cellulose K-100 LVP | 24.0 |
| 5 | Colloidal Silicon Dioxide | 0.75 |
| 6 | Magnesium Stearate | 3.0 |
| 7 | Lake Green Blend LB-51426 | 0.35 |
| | Total weight | 345 |

EXAMPLE 13

Color was mixed with some part of lactose and sifted through 100#mesh Alprazolam was mixed with lactose in geometric proportion and sifted through 40 mesh. HPMC K-4M and HPMC K-100 LVP are sifted through 40 mesh and mixed with above blend. This homogenous blend was granulated with water to form wet mass. Wet mass was dried and then crushed to form dried granules. Dried granules were lubricated and compressed to tablet with suitable punches.

Three tablets under study were prepared with the above procedure.

The tablets according to Example 13 are exactly similar to that of Example 4, except the addition of colour, which is optional. The colour is non-functional excipient with respect to the sustained release profile. Thus, for SR purposes, the Example 4 and Example 13 are same.

Experimental Procedure of Dissolution Test for the Comparative Study

The dissolution is carried out by using following parameters

TABLE 25

| Medium | Mixed Phosphate Buffer pH 6.0 ± 0.1 |
|---|---|
| Volume | 500 ml |
| Apparatus | USP I (Basket) |
| Speed | 100 rpm |
| Temperature | 37.0° C. |
| Time Interval | 1 Hr, 4 Hr, 8 Hr, 10 Hr, 12 Hr, 14 Hr, 18 Hr, 24 Hr. |
| Withdrawal volume | 5 ml |

Dissolution results of XANAX® (Alprazolam) XR of Pharmacia Upjohn.

Batch Number 63MCX (product in market); % Drug release.

TABLE 26

| Time Interval | Minimum | Maximum | Average | S.D. | % R.S.D. |
|---|---|---|---|---|---|
| 1 Hour | 11.52 | 12.75 | 12.32 | 0.46 | 3.73 |
| 4 Hour | 28.47 | 35.25 | 33.10 | 2.53 | 7.65 |
| 8 Hour | 48.41 | 57.54 | 55.01 | 3.42 | 6.22 |
| 10 Hour | 63.85 | 71.31 | 66.64 | 2.53 | 3.79 |
| 12 Hour | 70.25 | 77.41 | 72.98 | 2.48 | 3.40 |
| 14 Hour | 75.13 | 80.20 | 78.09 | 1.86 | 2.38 |
| 18 Hour | 82.55 | 94.45 | 87.70 | 4.37 | 4.98 |
| 24 Hour | 88.18 | 98.92 | 94.16 | 4.10 | 4.35 |

Dissolution results of Alprazolam Extended Release prepared as per Example 13; % Release

| Time Interval | Minimum | Maximum | Average | S.D. | % R.S.D. |
|---|---|---|---|---|---|
| 1 Hour | 10.78 | 11.23 | 10.99 | 0.23 | 2.06 |
| 4 Hour | 29.88 | 30.49 | 30.13 | 0.32 | 1.07 |
| 8 Hour | 48.73 | 50.13 | 49.60 | 0.76 | 1.53 |
| 10 Hour | 60.35 | 62.07 | 61.37 | 0.91 | 1.48 |
| 12 Hour | 69.21 | 71.44 | 70.39 | 1.12 | 1.59 |
| 14 Hour | 76.06 | 78.30 | 77.05 | 1.15 | 1.49 |
| 18 Hour | 83.52 | 85.99 | 84.81 | 1.24 | 1.46 |
| 24 Hour | 91.69 | 93.59 | 92.91 | 1.06 | 1.14 |

Comparative data of bioavailability of Alprazolam 3 mg extended release tablets of Pharmacia and Upjohn (XANAX® (Alprazolam) XR) vs Alprazolam 3 mg extended-release tablets of Emcure Pharmaceuticals.

EXAMPLE 14

Products Evaluated:

Test Product Alprazolam extended release tablet 3 mg according to the present invention (Example 4):

Reference Product: XANAX® (Alprazolam)XR tablets 3 mg. Pharmcia Upjohn Company, USA The experiment was carried out on 12 human subjects. One dose of either test or reference was administered orally. After the period of seven days, the another respective dose was administered orally such that the volunteer gets the dose of both test and reference.

Comparative data for concentration of Alprazolam in human plasma.

TABLE 27

| Time Data | Standard Deviation of Emcure's Test Sample (Product of Example 4) | Standard Deviation of XANAX® (Alprazolam) (95 MMJ) of Pharmacia Upjohn | Mean concentration of Emcure's test sample (Product of Example 4) ηg/ml |
|---|---|---|---|
| 0.00 | 0.139 | 0.182 | 0.040 |
| 3.00 | 5.141 | 4.877 | 19.323 |
| 6.00 | 5.890 | 6.463 | 23.452 |
| 9.00 | 7.081 | 7.359 | 26.171 |
| 12.00 | 5.282 | 5.154 | 25.510 |
| 16.00 | 4.818 | 5.598 | 22.429 |
| 20.00 | 5.123 | 5.734 | 19.728 |
| 24.00 | 5.369 | 5.746 | 18.547 |
| 36.00 | 4.086 | 5.083 | 10.924 |
| 48.00 | 3.491 | 4.385 | 6.819 |
| 72.00 | 2.110 | 2.233 | 2.823 |

It may be evident from examples 1-12 that the composition of examples 1-7 and 10-12 exhibit a release pattern, wherein the composition comprising alprazolam is released over a period of about 24 hours, i.e. between 20-40% in 4 hours to more than 70% in 40 hours of the total dose. Usually the $C_{max}$ is reached 3 hours after administration.

In examples 8 & 9, where only high viscosity HPMC or low viscosity HPMC are used, the release pattern vanes and is below the desirable standard. Further, from table 25 it is clear that XANAX® (Alprazolam) XR exhibits a large standard deviation in its release profile. Comparatively, the composition of the invention exhibits much less deviation, which shows that the peak-trough effect in case of the composition of the invention is negligible or non-existent.

According to the instant invention, the Alprazolam SR tablets are prepared as per Experiment Number 4. The dissolution experiments of the said tablets was carried out and compared with the tablets prepared as per the compositions known in the prior art.

The experimental procedure and results of the above experiments is provided below in Table-28 and Table-29.

TABLE 28

(Compositions known in prior art)

| SERIAL NUMBER | INGREDIENTS | WEIGHT (mg) |
|---|---|---|
| 1 | Alprazolam | 3.0 |
| 2 | Lactose monohydrate (Lactose DCL 11) | 221.7 |
| 3 | Hydroxy Propyl Methyl Cellulose K-4M | 60.0 |
| 4 | Hydroxy Propyl Methyl Cellulose K-100 LVP | 60.6 |
| 5 | Colloidal Silicon Dioxide | 0.75 |
| 6 | Magnesium Stearate | 1.5 |

TABLE 28-continued (Compositions known in prior art)

| SERIAL NUMBER | INGREDIENTS | WEIGHT (mg) |
|---|---|---|
| 7 | D & C Yellow # 10 | 0.24 |
| 8 | FD&C Blue # 2 Aluminum Lake | 0.06 |
| | Total weight | 348.6 |

EXAMPLE 15

Color was mixed with some part of lactose and sifted through 100 # mesh Alprazolam was mixed with lactose in geometric proportion and sifted through 40 mesh. This was added to the above blend. HPMC K-4M and HPMC K-100 LVP are sifted through 40 mesh and mixed with above blend. Colloidal silicon dioxide was sifted through 40 #. Magnesium stearate was also sifted through 40 # and both were mixed to the above blend. The entire blend was compressed to tablet with suitable punch.

Three tablets under study were prepared with the above procedure.

Experimental Procedure of Dissolution Test for the Comparative Study.

The dissolution is carried out by using following parameters

TABLE 25

| Medium | Mixed Phosphate Buffer pH 6.0 ± 0.1 |
|---|---|
| Volume | 500 ml |
| Apparatus | USP I (Basket) |
| Speed | 100 rpm |
| Temperature | 37.0° C. |
| Time Interval | 1 Hr, 4 Hr, 8 Hr, 10 Hr, 12 Hr, 14 Hr, 18 Hr, 24 Hr. |
| Withdrawal volume | 5 ml |

Dissolution results of XANAX® (Alprazolam) XR of Pharmacia Upjohn

Batch Number 63 MCX (Product in market); % Drug release.

TABLE 26

| Time Interval | Minimum | Maximum | Average | S.D. | % R.S.D. |
|---|---|---|---|---|---|
| 1 Hour | 11.52 | 12.75 | 12.32 | 0.46 | 3.73 |
| 4 Hour | 28.47 | 35.25 | 33.10 | 2.53 | 7.65 |
| 8 Hour | 48.41 | 57.54 | 55.01 | 3.42 | 6.22 |
| 10 Hour | 63.85 | 71.31 | 66.64 | 2.53 | 3.79 |
| 12 Hour | 70.25 | 77.41 | 72.98 | 2.48 | 3.40 |
| 14 Hour | 75.13 | 80.20 | 78.09 | 1.86 | 2.38 |
| 18 Hour | 82.55 | 94.45 | 87.70 | 4.37 | 4.98 |
| 24 Hour | 88.18 | 98.92 | 94.16 | 4.10 | 4.35 |

Dissolution results of Alprazolam Extended Release prepared as per Example 13; % Release

TABLE 29

| Time Interval | Minimum | Maximum | Average | S.D. | % R.S.D. |
|---|---|---|---|---|---|
| 1 Hour | 10.78 | 11.23 | 10.99 | 0.23 | 2.06 |
| 4 Hour | 29.88 | 30.49 | 30.13 | 0.32 | 1.07 |
| 8 Hour | 48.73 | 50.13 | 49.60 | 0.76 | 1.53 |
| 10 Hour | 60.35 | 62.07 | 61.37 | 0.91 | 1.48 |
| 12 Hour | 69.21 | 71.44 | 70.39 | 1.12 | 1.59 |
| 14 Hour | 76.06 | 78.30 | 77.05 | 1.15 | 1.49 |

TABLE 29-continued

| Time Interval | Minimum | Maximum | Average | S.D. | % R.S.D. |
|---|---|---|---|---|---|
| 18 Hour | 83.52 | 85.99 | 84.81 | 1.24 | 1.46 |
| 24 Hour | 91.69 | 93.59 | 92.91 | 1.06 | 1.14 |

Dissolution results of Alprazolam Extended Release (Prior art US 2004/0006072) Batch Number AZM/05/029; % Release

| Time Interval | Minimum | Maximum | Average | S.D. | % R.S.D. |
|---|---|---|---|---|---|
| 1 Hour | 12.00 | 14.10 | 13.60 | 0.40 | 3.00 |
| 4 Hour | 31.00 | 36.10 | 34.90 | 0.80 | 2.30 |
| 8 Hour | 47.90 | 59.30 | 57.20 | 4.70 | 8.20 |
| 10 Hour | 59.40 | 73.00 | 68.40 | 6.80 | 9.90 |
| 12 Hour | 68.30 | 80.50 | 77.10 | 8.30 | 10.00 |
| 14 Hour | 82.70 | 90.00 | 86.40 | 8.30 | 10.00 |
| 18 Hour | 90.50 | 98.10 | 92.90 | 3.60 | 3.90 |
| 24 Hour | 95.40 | 101.50 | 95.00 | 3.30 | 3.50 |

We claim:

1. A sustained release pharmaceutical composition comprising:
   (a) a therapeutically effective amount of alprazolam,
   (b) a high viscosity hydroxy-propyl-methyl cellulose (HPMC) and low viscosity hydroxy-propyl-methyl cellulose (HPMC), wherein the total amount of HPMC is about 70 mg to about 100 mg in a ratio of 70:30 to 85:15, and
   (c) pharmaceutically acceptable excipients.

2. A composition as claimed in claim 1, wherein the amount of alprazolam is between 1 mg and 5 mg.

3. A composition as claimed in claim 1, wherein the alprazolam is a pharmaceutically acceptable salt of alprazolam.

4. A composition as claimed in claim 1, wherein the high viscosity HPMC has about 19% to about 24% by weight of methoxy substituent, and about 4% to about 12% by weight of hydroxypropoxy substituent.

5. A composition as claimed in claim 1, wherein the high viscosity HPMC has a viscosity of about 1500 to about 2,25,000 cp.

6. A composition as claimed in claim 1, wherein the low viscosity HPMC has a viscosity of about 2 to about 400 cp.

7. A composition as claimed in claim 1, wherein the low viscosity HPMC is selected from the group consisting of K3 P LV and K 100P LV.

8. A composition as claimed in claim 1, wherein the ratio of high viscosity HPMC to low viscosity HPMC is 65:35 to 75:25.

9. A composition as claimed in claim 1, wherein the ratio of high viscosity HPMC to low viscosity HPMC is 70:30.

10. A composition as claimed in claim 1, wherein the composition provides a total daily dose of about 0.5 mg to about 3 mg of alprazolam.

11. A composition as claimed in claim 1, wherein the composition is configured to release alprazolam at a rate that ranges between 20% to 40% in 4 hours to more than 70% in 14 hours of the total dose of alprazolam after the exposure to phosphate buffer having pH 6.0.+−.0.1.

12. A composition as claimed in claim 1, wherein the $C_{max}$ occurs more than 3 hours after administration.

13. A process for the preparation of a sustained release composition of alprazolam, comprising the steps of:
   (a) mixing alprazolam with lactose and optionally coloring agents in geometric proportion;

(b) sifting the mixture to obtain homogeneous blend;
(c) adding a high viscosity hydroxy-propyl-methyl cellulose (HPMC) and low viscosity hydroxy-propyl-methyl cellulose (HPMC), wherein the total amount of HPMC is about 70 mg to about 100 mg in a ratio of 70:30 to 85:15 to the blend from step (b);
(d) granulating the blend with water to form wet mass;
(e) drying the wet mass;
(f) forming granules; and
(g) compressing to form tablet.

* * * * *